United States Patent
Parmigiani

(10) Patent No.: US 9,731,078 B2
(45) Date of Patent: Aug. 15, 2017

(54) SYRINGE FOR INJECTING SOLID GRANULAR MATERIAL

(71) Applicant: C.G.M. S.P.A., Correggio, Reggio Emilia (IT)

(72) Inventor: Corrado Saverio Parmigiani, Reggio Emilia (IT)

(73) Assignee: C.G.M. S.P.A., Correggio (Reggio Emilia) (IT)

( * ) Notice: Subject to any disclaimer, the term of this patent is extended or adjusted under 35 U.S.C. 154(b) by 260 days.

(21) Appl. No.: 14/385,108

(22) PCT Filed: Mar. 1, 2013

(86) PCT No.: PCT/IB2013/000405
§ 371 (c)(1),
(2) Date: Sep. 12, 2014

(87) PCT Pub. No.: WO2013/136168
PCT Pub. Date: Sep. 19, 2013

(65) Prior Publication Data
US 2015/0037752 A1 Feb. 5, 2015

(30) Foreign Application Priority Data
Mar. 14, 2012 (IT) .............................. RE2012A0020

(51) Int. Cl.
*A61M 5/178* (2006.01)
*A61M 5/315* (2006.01)
(Continued)

(52) U.S. Cl.
CPC ........... *A61M 5/31513* (2013.01); *A61C 5/62* (2017.02); *A61B 17/8825* (2013.01); *A61C 19/06* (2013.01)

(58) Field of Classification Search
CPC ........... A61C 5/062; A61C 6/064; A61C 5/06; A61M 37/0069; A61M 5/3015;
(Continued)

(56) References Cited

U.S. PATENT DOCUMENTS

| 4,472,141 A * | 9/1984 | Dragan | ............... A61C 5/062 222/386 |
| 4,676,655 A * | 6/1987 | Handler | ............... B01F 11/0054 222/129 |

(Continued)

FOREIGN PATENT DOCUMENTS

| EP | 2050509 A1 | 4/2009 |
| JP | 2001057987 A | 3/2001 |

(Continued)

OTHER PUBLICATIONS

International Standard ISO 594-2, Second Edition Sep. 1, 1998, Conical fittings with 6% (Luer) taper for syringes, needles and certain other medical equipment—Part 2:Lock fittings.*

*Primary Examiner* — Nathan R Price
*Assistant Examiner* — John Doubrava
(74) *Attorney, Agent, or Firm* — Volpe and Koenig, P.C.

(57) ABSTRACT

A syringe for injecting solid, hard and rough granular material includes: a longitudinal injection chamber having constant section and an internal diameter of less than 4.5 mm, having a distal outlet mouth for the flow out of the material, whose surface is the same as the injection chamber, and a proximal mouth, in which granular material is inserted; a plunger sealedly mobile along the injection chamber, joined to a stem which enters the injection chamber through the proximal mouth, the plunger having: a transversal section which sealingly couples with the surface of the injection chamber, and having an operative surface, facing towards the distal mouth of the injection chamber; and a body projecting longitudinally internally of the injec- (Continued)

tion chamber, fixed substantially axially to the operating surface of the plunger, having a diameter that is less than 70% of that of the injection chamber and a length greater than 6 mm.

5 Claims, 4 Drawing Sheets

(51) Int. Cl.
*A61C 5/62* (2017.01)
*A61B 17/88* (2006.01)
*A61C 19/06* (2006.01)

(58) Field of Classification Search
CPC .......... A61M 2005/3158; A61M 5/315; B05C 17/005; A61F 2/4604
USPC ................. 604/58, 57, 59, 218, 187; 433/58
See application file for complete search history.

(56) References Cited

U.S. PATENT DOCUMENTS

| | | | | |
|---|---|---|---|---|
| 4,769,011 A * | 9/1988 | Swaniger | A61M 37/0069 | 604/218 |
| 4,801,263 A * | 1/1989 | Clark | A61C 5/062 | 433/90 |
| 5,181,918 A * | 1/1993 | Brandhorst | A61M 5/31513 | 604/187 |
| 6,019,765 A * | 2/2000 | Thornhill | A61F 2/4601 | 606/93 |
| 6,267,749 B1 * | 7/2001 | Miklos | A61M 5/5013 | 604/110 |
| 6,398,763 B1 * | 6/2002 | Richardson | A61C 5/062 | 604/218 |
| 6,620,169 B1 * | 9/2003 | Peterson | A61B 17/8833 | 606/93 |
| 7,112,205 B2 * | 9/2006 | Carrison | A61B 17/3472 | 606/92 |
| 7,306,611 B2 * | 12/2007 | Cirotteau | A61B 17/7095 | 222/387 |
| 7,357,789 B2 * | 4/2008 | Bills | A61C 5/062 | 604/187 |
| 7,503,905 B2 * | 3/2009 | Jessop | A61C 5/062 | 604/122 |
| 8,852,200 B2 * | 10/2014 | Steffen | A61B 17/8822 | 606/93 |
| 8,870,888 B2 * | 10/2014 | Steffen | A61B 17/8827 | 606/94 |
| 2002/0098462 A1 * | 7/2002 | Kaneko | A61C 5/062 | 433/89 |
| 2002/0099384 A1 * | 7/2002 | Scribner | A61B 17/1631 | 606/92 |
| 2004/0068234 A1 * | 4/2004 | Martin | A61B 17/7095 | 604/187 |
| 2004/0078006 A1 * | 4/2004 | Bills | A61C 3/005 | 604/221 |
| 2006/0264964 A1 * | 11/2006 | Scifert | A61B 17/8816 | 606/92 |
| 2007/0100291 A1 * | 5/2007 | Huang | A61M 5/322 | 604/198 |
| 2008/0300550 A1 * | 12/2008 | Schiller | A61M 5/31511 | 604/220 |
| 2009/0255960 A1 * | 10/2009 | Keller | A61B 17/00491 | 222/386 |
| 2009/0289084 A1 * | 11/2009 | Kunishi | A61C 5/062 | 222/386 |
| 2011/0015574 A1 * | 1/2011 | Persat | A61B 17/3472 | 604/113 |
| 2011/0034882 A1 * | 2/2011 | Quinn | A61M 5/31511 | 604/218 |
| 2011/0092903 A1 * | 4/2011 | Caizza | A61M 5/502 | 604/110 |
| 2012/0258420 A1 * | 10/2012 | Boehm | A61C 5/062 | 433/89 |
| 2013/0126559 A1 * | 5/2013 | Cowan | A61M 5/31525 | 222/333 |
| 2014/0094749 A1 * | 4/2014 | Cowan | A61M 5/315 | 604/93.01 |
| 2014/0148781 A1 * | 5/2014 | Tekeste | A61M 5/3134 | 604/506 |
| 2014/0276581 A1 * | 9/2014 | Lou | A61B 17/8822 | 604/506 |
| 2015/0125827 A1 * | 5/2015 | Claypool | A61C 5/062 | 433/226 |
| 2015/0209521 A1 * | 7/2015 | Titus | A61M 5/31511 | 604/218 |
| 2016/0030284 A1 * | 2/2016 | Vedrine | A61J 1/1412 | 220/367.1 |

FOREIGN PATENT DOCUMENTS

| | | |
|---|---|---|
| JP | 2006204628 A | 8/2006 |
| JP | 2008018974 A | 1/2008 |

* cited by examiner

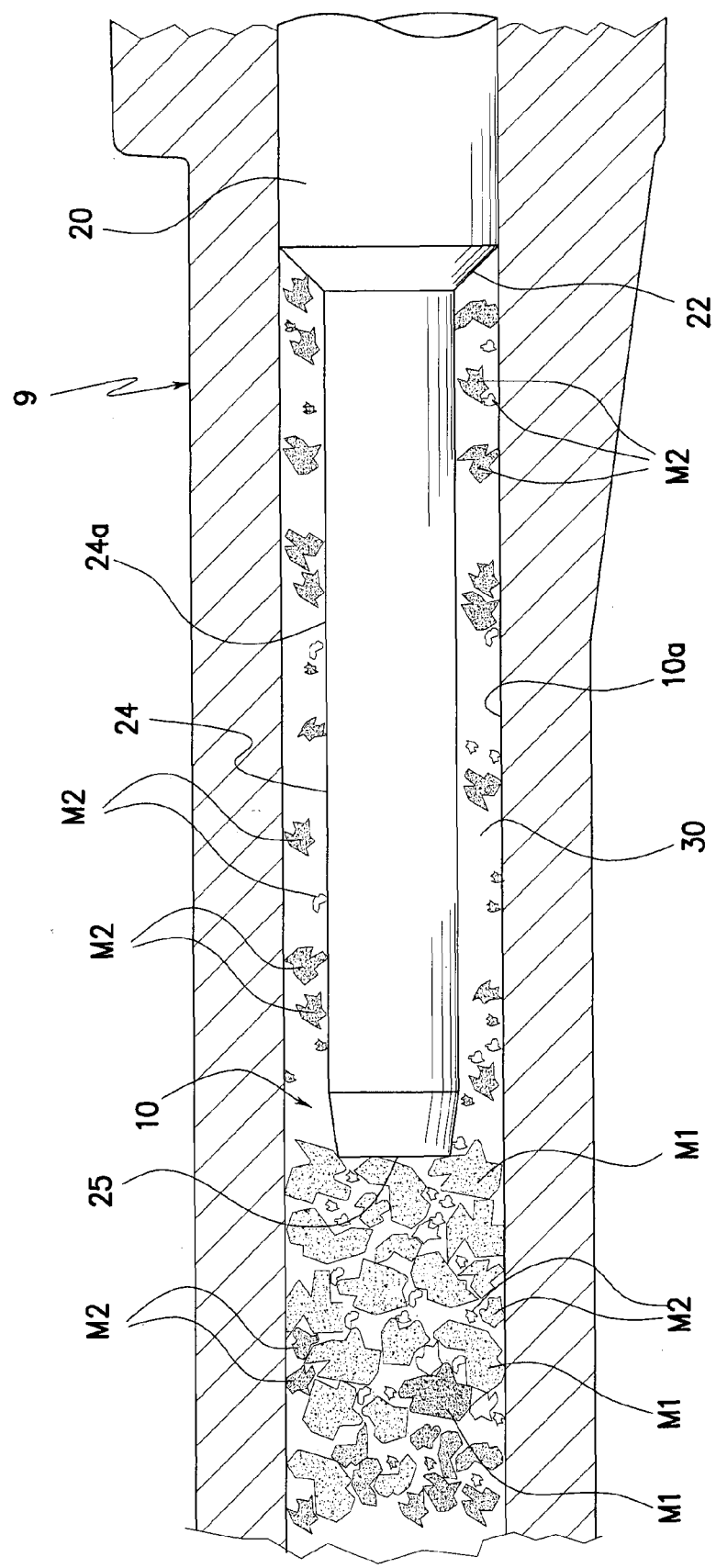

SYRINGE FOR INJECTING SOLID GRANULAR MATERIAL

FIELD OF THE INVENTION

The present invention relates to a syringe for injecting solid hard and rough granular material, in particular a syringe used in surgical applications, especially in dental implant surgery and oro-maxillofacial surgery, suitable for injecting granular material for reconstructing bone tissue.

BACKGROUND

One of the techniques for reconstructing damaged bone tissue, which has been in use for some time, comprises the use of bio-compatible materials able to facilitate growth of the tissue. These materials are mainly divided into two categories, Hydroxylapatites and Tricalcium-phosphates which represent the minerals which constitute human bones.

These materials are typically produced artificially and distributed in the form of highly-porous granules such as to facilitate, internally of the porosities thereof, formation of osteocytes, i.e. cells which constitute bone tissue.

As described in patent publications U.S. Pat. No. 4,769,011, U.S. Pat. No. 4,801,263 and U.S. Pat. No. 7,357,789, present methods comprise use of devices, substantially syringes, suitable for injecting these granules into cavities in which bone tissue is to be reconstructed.

These devices therefore comprise an injection chamber having a distal outlet mouth for the material and a proximal mouth, in which the granular material is inserted, and a plunger, which sealedly slides along the injection chamber, having an operating surface facing the distal mouth of the injection chamber, destined to push the material along the injection chamber.

As demonstrated also in U.S. Pat. No. 4,801,263, there exists a need to realise injection chambers having relatively very small geometric dimensions (i.e. having a diameter of the injection chamber of a few millimeters), such as to ensure a good handlability by the surgeon, while at the same time being capable of realising the exiting of the material from the distal mouth.

In effect, the porous and consequently rough nature of the material, together with the geometric irregularities of the granules, facilitate the formation of agglomerates which can constitute occlusions of the injection chamber and the distal mouth. Further, the substantially ceramic and therefore hard nature of the material constitute a highly abrasive agent against the walls of the chamber. This abrasive action adversely affects the flowability of the granulate itself.

The need for easy handling of the syringe and the requirement of operating on small-dimension fractures and lacerations induce designers to reduce the section of the injection chamber; on the other hand, the smaller the section of the injection chamber, the worse the flowability of the granulate; consequently the section of the injection chamber cannot fall below critical values without entailing a high risk of agglomeration and formation of blockages which in fact prevent the sliding of the plunger and therefore the exit of the granulate from the syringe.

The granular material currently used has a particle size of between 0.1 mm and 1.5 mm in diameter, while an optimal size of the syringes, such as to facilitate their handling, is 4.5 mm in diameter. This size represents a critical value since for higher values the risk of formation of occlusions is substantially zero while for values lower than the risk of compacting is very high. The formation of occlusions by the material remains one of the main unresolved drawbacks in the prior art.

SUMMARY

An objective of the present invention is to obviate the mentioned technical drawback, by providing a syringe in which, while the injection chamber has a diameter of smaller than 4.5 mm, making it possible to inject granular material containing granules having a diameter of between 0.1 and 1.5 mm.

according to another aspect of the invention, its purpose is to implement in a simple and effective way the injection of solid, hard and rough granular of Hydroxylapatites and Tricalcium-phosphates material, having diameters comprised between 0.1 and 1.5 mm, through an injection chamber (10) having internal constant diameter of less than 4.5 mm.

This and other aims are attained by the present invention, as it is characterised in the claims.

BRIEF DESCRIPTION OF THE DRAWINGS

The invention is described in detail in the following with the aid of the accompanying figures which illustrate an embodiment thereof by way of non-exclusive example.

FIG. 4 is a larger-scale drawing of a detail of FIG. 3.

DETAILED DESCRIPTION OF THE PREFERRED EMBODIMENTS

Figure 1:
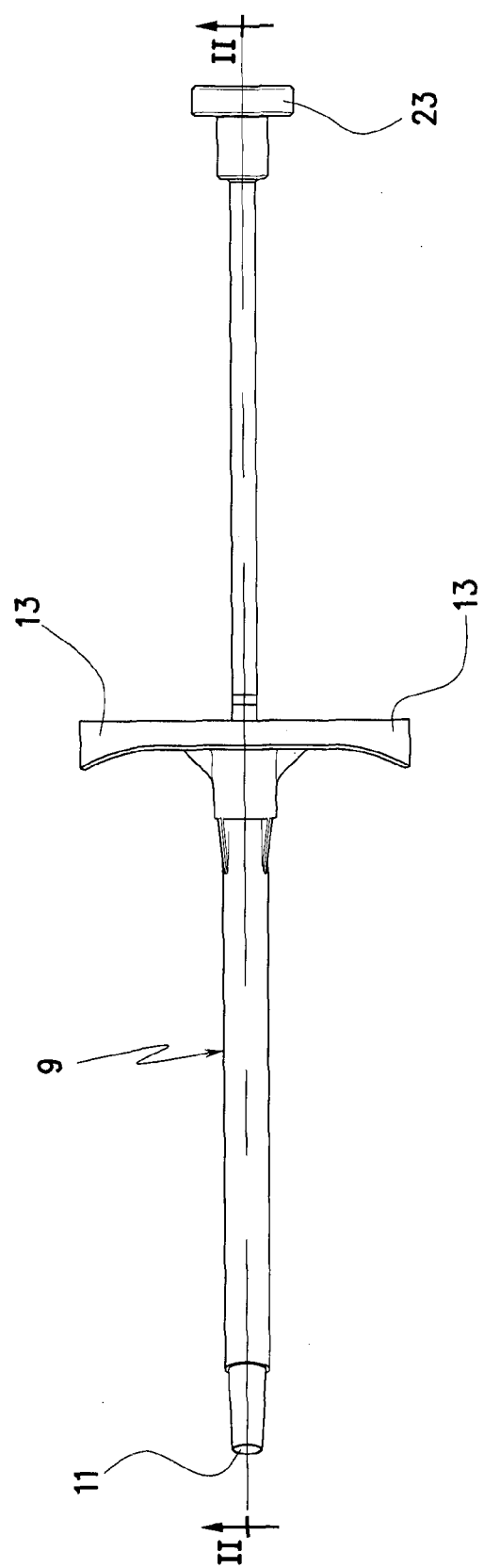
FIG. 1 is a view from above of the syringe.
Figure 2:
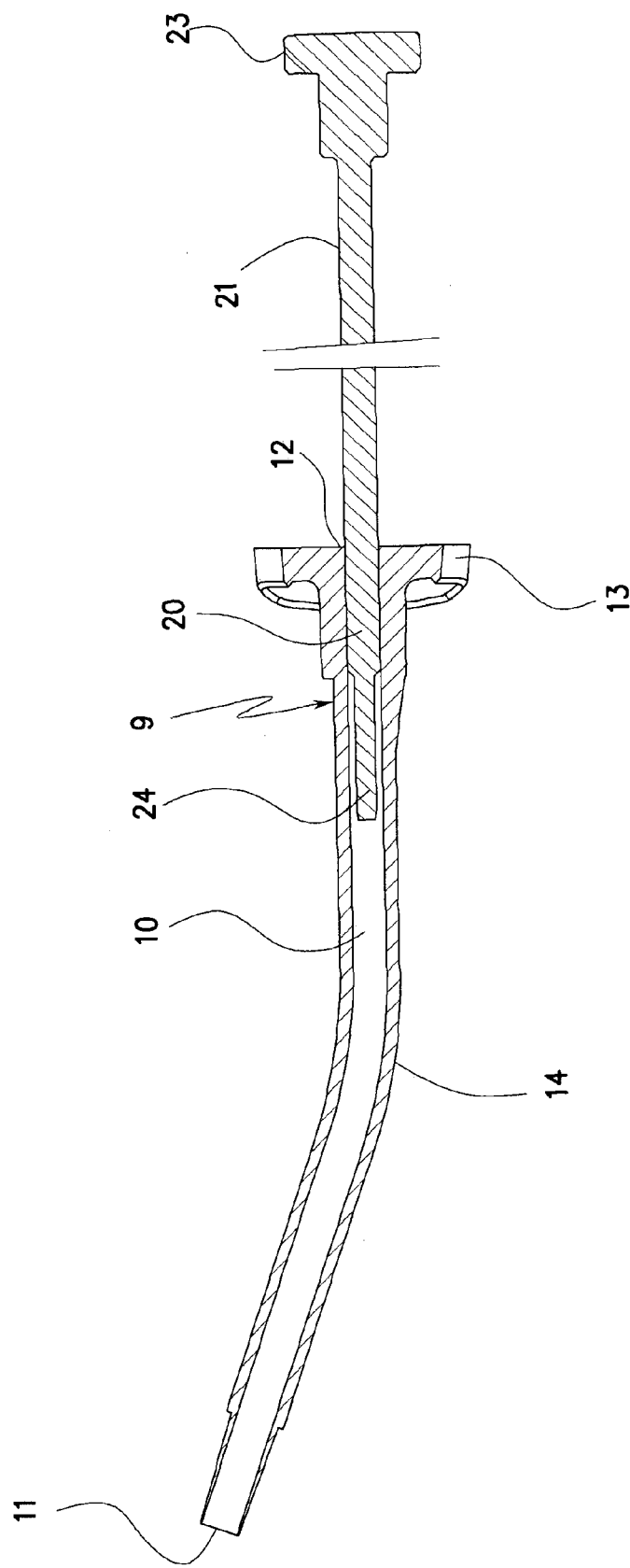
FIG. 2 is a section along plane II-II of FIG. 1.
Figure 3:
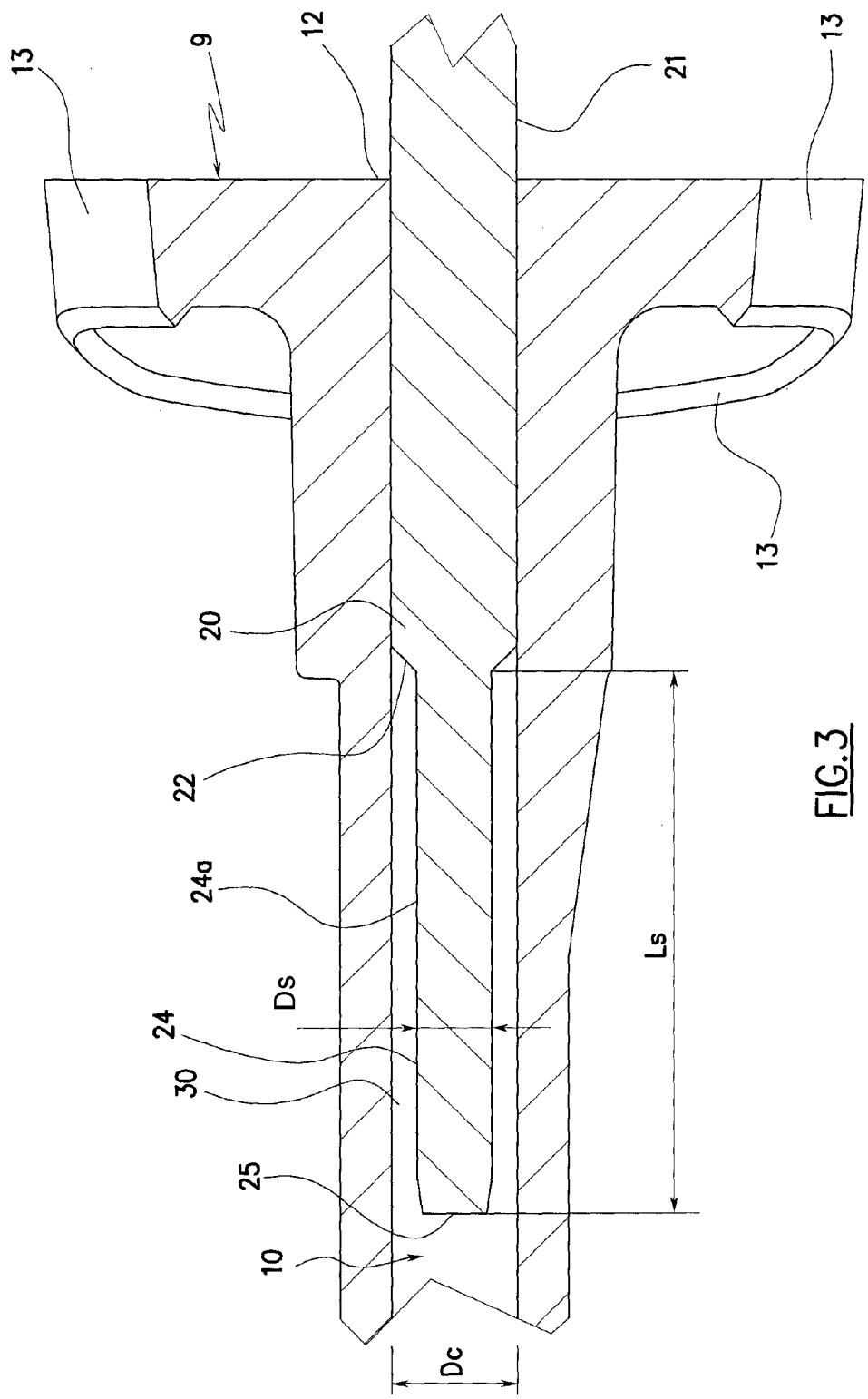
FIG. 3 is a larger-scale drawing of a detail of FIG. 2.

The syringe for injecting solid hard and rough granular material comprises a tubular body 9, in which a longitudinal injection chamber 10 is afforded, having constant section and an inside diameter Dc of less than 4.5 mm, and having a distal exit mouth 11 for the flow out of the material, whose surface is the same as the injection chamber (10), and a proximal mouth 12.

Granular material comprising granules having a diameter between 0.1 and 1.5 mm is inserted in the injection chamber 10.

According to a preferred embodiment, the tubular body 9 comprises two transversal protuberances 13 at the proximal mouth 12, which develop more or less radially towards the outside of the injection chamber 10, suitable for facilitating the gripping of the body 9 by the operator's fingers. For example in this way the operator can grip the syringe with the proximal mouth 12 facing the palm of the hand and squeeze the tubular body 9 between the index finger and middle finger of the same hand, which in turn grip the protuberances.

The injection chamber 10 extends longitudinally with a much greater length than the diameter Dc. Further, in the embodiment illustrated in the figures, the chamber 10 has a curvature 14 substantially at the midpoint of this length; in this way the syringe is easier to handle and able to reach, with its distal mouth end 11, sites or cavities in positions that are not easily accessible, enabling the operator to perform even particularly complex operations.

According to the embodiment shown in the figures, at the distal mouth end 11 the external surface of the tubular body 9 exhibits a tapered shape in which the external diameter of the tubular body 9 decreases until it almost reaches the value of the diameter Dc of the chamber at the distal mouth end 11.

The syringe further comprises a plunger 20 that is mobile along the injection chamber 10, with a sealed sliding along the inner surface 10a of the chamber itself, joined to a stem 21 which enters into the injection chamber through the proximal mouth 12.

The stem 21 is advantageously flexible so that it can slide internally of the injection chamber 10 following the curvature 14 thereof. Consequently a good material for the realization of the invention is propylene because it is a low-cost material, processable by injection moulding and having excellent mechanical characteristics.

The plunger 20 has a transversal section that sealingly couples with the surface of the injection chamber 10, that is to say which has a substantially equal diameter to the diameter Dc of the injection chamber.

Further, the plunger 20 has an operating surface 22, facing the distal mouth 11 of the injection chamber 10, acting against the material located within the chamber and suitable for pushing it along the entire chamber, up to the distal mouth 11.

According to the illustrated embodiment, the stem 21 has a section that is substantially equal to the section of the plunger 20 and is made in a single body there-with. Therefore, the plunger 20 is substantially defined by the distal end portion of a body composed of the plunger 20 and stem 21.

At the proximal end thereof, opposite the operating surface 22, the stem 21 includes a button 23 having a larger diameter such as to define a suitable thrust surface suitable for pressing by an operator's finger.

The plunger 20 comprises a projecting body 24, substantially cylindrical in shape, which extends longitudinally projectingly forwards inside the injection chamber 10, fixed substantially axially to the operating surface 22 of the plunger 20, having a frontal operating end 25. The diameter Ds of the body 24 is less than 70% of the diameter Dc of the chamber 10 and the length Ls is greater than 6 mm.

A tubular space 30 is defined between the lateral surface 24a of the projecting body 24 and the internal surface 10a of the injection chamber 10.

In use, first the granular material, in particular hydroxyapatite and Tri-Calcium Phosphate, is introduced into the injection chamber 10, in methods for the reconstruction of damaged bone tissue, possibly together with a physiological fluid.

FIG. 4 schematically illustrates the granules of material introduced into the chamber 10: M1 denotes the granules of greater dimensions and M2 the granules of smaller dimensions.

When the operator, by pressing the button 23, applies a longitudinal thrust on the plunger 20, the plunger 20 translates longitudinally along the chamber 10, pushing the granular material along the chamber itself up to the distal mouth 11.

According to the traditional techniques, this translation is, however, hampered by the fact that the granules of material, M1 and M2, in particular in the case where the granules are hydroxyapatites and Tricalcium Phosphate, which have a porous structure and are consequently rough and have considerable geometric irregularities, are bound mechanically to each other and form agglomerates with a rather rigid structure that, normally, having a high abrasive power, create a high level of friction against the internal surface of the chamber 10 and thus block the movement of the plunger toward the distal mouth 11.

It has surprisingly been found that the presence of the projecting body 24 is able to remove these occlusions, by nudging the granules of the material forming the agglomerates and thus enabling the plunger to slide smoothly along the entire injection chamber 10.

An explanation of the phenomenon is that as the diameter Ds of the projecting body 24 is less than the diameter Dc of the operating surface 22, the thrust acting on the material by the plunger 20 is concentrated on the front end 25, producing a much greater pressure than that which would be exerted by the operating surface 22 of the plunger 20, given a same force applied by the operator.

Further, by acting only in the central area of the agglomerate, the end 25 of the body 24 removes the granules located in the central area of the room as it advances, removing and then disassembling the structure of the agglomerate, and then cancelling or at least reducing the frictional action that the material forms against the internal surface 10a of the chamber 10.

It has also been found that the efficiency of the projecting body 24 in the removal of the occlusions increases together with the decreasing of its diameter Ds; in the preferred embodiment the projecting body 24 has a diameter Ds of 20-50% of the diameter Dc of the injection chamber 10. Naturally, the decrease in the diameter Ds cannot be such as to excessively reduce the mechanical strength of the projecting body 24.

It has also been found that, in order to be efficient, the projecting body 24 must have a relatively significant length Ls, which in any case should be greater than 6 mm.

The length Ls cannot, however, be too great, including for structural reasons, and therefore in the preferred embodiment the projecting body 24 has a total length Ls of between 10 mm and 15 mm.

Furthermore, in the preferred embodiment the projecting body 24 comprises an initial portion having a constant diameter, starting from the operating surface of the plunger, over 80% of its length Ls. In the remaining part, the body 24 can exhibit a truncoconical end profile suitable for facilitating the effect of removing the occlusions.

Obviously numerous modifications of a practical-applicational nature can be made to the invention without its thereby forsaking from the scope of the inventive idea as claimed below.

What is claimed is:

1. A syringe for injecting solid, hard and rough granular material, having diameters between 0.1 and 1.5 mm, comprising:
   a tubular body (9) provided with a longitudinal injection chamber (10) having constant section and an internal diameter (Dc) of less than 4.5 mm, the injection chamber having:
   a distal outlet mouth (11) for the flowing of the material out of the injection chamber, the distal outlet mouth (11) being at the end of the injection chamber and at the end of the tubular body (9), the distal outlet mouth (11) having the same inner diameter as the injection chamber (10), and
   a proximal mouth (12) at the other end of the injection chamber and at the other end of the tubular body (9), in which granular material is inserted;
   a plunger (20), sealedly mobile along the whole injection chamber (10), until the distal mouth (11), joined to a stem (21) which enters the injection chamber (10) through the proximal mouth,
   the plunger (20) having a transversal section which sealingly couples with the surface of the injection chamber (10), and having an operative surface (22), facing towards the distal mouth (11) of the injection chamber (10), suitable for pushing the material along the injection chamber (10), wherein the plunger (20) comprises a body (24) projecting longitudinally internally of the injection chamber (10), fixed substantially axially to the operating surface (22) of the plunger (20), having a diameter (Ds) that is less than 70% of the diameter (Dc) of the injection chamber (10) and a length (Ls) that is greater than 6 mm.

2. The syringe of claim 1, wherein the projecting body (24) has a diameter (Ds) that is 20-50% of the diameter (Dc) of the injection chamber (10).

3. The syringe of claim 1, wherein the projecting body (24) has a total length (Ls) comprised between 10 mm and 15 mm.

4. The syringe of claim 1, wherein the projecting body (24) comprises an initial tract having a constant diameter, starting from the operating surface (22) of the plunger, for a length that is 80% of a length thereof (Ls).

5. Method for injecting solid, hard and rough granular Hydroxylapatites and Tricalcium-phosphates material, having diameters comprised between 0.1 and 1.5 mm, the method comprising:

providing a syringe containing the material to be injected, wherein the syringe comprises:

a tubular body (9) provided with a longitudinal injection chamber (10) having internal constant section and a diameter (Dc) of less than 4.5 mm, having a distal outlet mouth (11) for the flow out of the material, the distal outlet mouth (11) being at the end of the injection chamber (10) and at the end of the tubular body (9), the distal outlet mouth (11) having an inner diameter having the same inner diameter as the injection chamber (10), and a proximal mouth (12) at the other end of the injection chamber and at the other end of the tubular body (9), in which granular material is inserted;

a plunger (20), sealedly mobile along the injection chamber (10), joined to a stem (21) which enters the injection chamber (10) through the proximal mouth, the plunger (20) having a transversal section which sealingly couples with the surface of the injection chamber (10), and having an operative surface (22), facing towards the distal outlet mouth (11) of the injection chamber (10), suitable for pushing the material along the injection chamber (10), the syringe further comprises a body (24) projecting longitudinally internally of the injection chamber (10), fixed substantially axially to the operating surface (22) of the plunger (20), having a diameter (Ds) that is less than 70% of the diameter (Dc) of the injection chamber (10) and a length (Ls) that is greater than 6 mm; and injecting the solid, hard and rough granular Hydroxypatites and Tricalcium-phosphates material contained in the syringe.

* * * * *